United States Patent
Zubok et al.

(10) Patent No.: US 8,070,814 B2
(45) Date of Patent: *Dec. 6, 2011

(54) ARTIFICIAL INTERVERTEBRAL DISC HAVING AN ARTICULATING JOINT

(75) Inventors: Rafail Zubok, Midland Park, NJ (US); Michael W. Dudasik, Nutley, NJ (US); Joseph P. Errico, Green Brook, NJ (US)

(73) Assignee: SpineCore, Inc., Allendale, NJ (US)

( * ) Notice: Subject to any disclaimer, the term of this patent is extended or adjusted under 35 U.S.C. 154(b) by 472 days.

This patent is subject to a terminal disclaimer.

(21) Appl. No.: 12/228,435

(22) Filed: Aug. 13, 2008

(65) Prior Publication Data

US 2009/0048674 A1    Feb. 19, 2009

Related U.S. Application Data

(63) Continuation of application No. 11/708,813, filed on Feb. 20, 2007, now Pat. No. 7,452,380, which is a continuation of application No. 11/056,064, filed on Feb. 11, 2005, now Pat. No. 7,214,244.

(60) Provisional application No. 60/546,027, filed on Feb. 19, 2004.

(51) Int. Cl.
  *A61F 2/44* (2006.01)

(52) U.S. Cl. .................... 623/17.13; 623/17.14

(58) Field of Classification Search ..... 623/17.11–17.16
See application file for complete search history.

(56) References Cited

U.S. PATENT DOCUMENTS

| | | | |
|---|---|---|---|
| 4,997,432 A | 3/1991 | Keller | |
| 5,314,477 A | 5/1994 | Marnay | |
| 5,370,697 A | 12/1994 | Baumgartner | |
| 5,425,773 A | 6/1995 | Boyd et al. | |
| 5,507,816 A | 4/1996 | Bullivant | |
| 5,676,701 A | 10/1997 | Yuan et al. | |
| 5,676,702 A | 10/1997 | Ratron | |
| 5,683,465 A | 11/1997 | Shinn et al. | |
| 5,782,832 A | 7/1998 | Larsen et al. | |
| 5,893,889 A | 4/1999 | Harrington | |
| 5,895,428 A | 4/1999 | Berry | |
| 5,899,941 A | 5/1999 | Nishijima et al. | |
| 5,989,291 A | 11/1999 | Ralph et al. | |
| 6,019,792 A | 2/2000 | Cauthen | |
| 6,368,350 B1 | 4/2002 | Erickson et al. | |
| 6,989,032 B2 | 1/2006 | Errico et al. | |

(Continued)

OTHER PUBLICATIONS

Office Action from Corresponding Japanese Application 2006-554171, dated Nov. 10, 2009.

(Continued)

*Primary Examiner* — Bruce E Snow
(74) *Attorney, Agent, or Firm* — Lerner, David, Littenberg, Krumholz & Mentlik, LLP

(57) ABSTRACT

An intervertebral device includes a first plate having an outer face and an inner face, and a second plate juxtaposed with the first plate, the second plate having an outer face, an inner face that opposes the first plate and a concavity that opposes the first plate. The device includes an elongated member extending from the first plate toward the second plate, the elongated member having a distal end with a spherical surface that is engageable with the concavity of the second plate for providing an articulating joint between the first and second plates. The device also includes a resilient member in contact with the elongated member for counteracting compressive loads on the plates, the resilient member being surrounded by the concavity of the second plate.

22 Claims, 5 Drawing Sheets

U.S. PATENT DOCUMENTS

| | | |
|---|---|---|
| 7,214,244 B2 | 5/2007 | Zubok et al. |
| 7,452,380 B2 * | 11/2008 | Zubok et al. ............... 623/17.14 |
| 2002/0128714 A1 | 9/2002 | Manasas et al. |
| 2003/0014112 A1 | 1/2003 | Ralph et al. |
| 2003/0040802 A1 | 2/2003 | Errico et al. |
| 2005/0251260 A1 | 11/2005 | Gerber et al. |

* cited by examiner

ARTIFICIAL INTERVERTEBRAL DISC HAVING AN ARTICULATING JOINT

CROSS REFERENCE TO RELATED APPLICATIONS

This application is a continuation of U.S. application Ser. No. 11/708,813, filed Feb. 20, 2007, now allowed, which is a continuation of U.S. Pat. No. 7,214,244, filed Feb. 11, 2005, which claims the benefit of U.S. Provisional Application No. 60/546,027, filed Feb. 19, 2004, the disclosures of which are hereby incorporated herein by reference.

BACKGROUND OF THE INVENTION

This invention relates generally to a spinal implant assembly for implantation into the intervertebral space between adjacent vertebral bones to simultaneously provide stabilization and continued flexibility and proper anatomical motion, and more specifically to such a device that has limited rotation using an uncaptured ball and socket joint with a partial ball having a large radius and substantially continuous radii of curvature.

The bones and connective tissue of an adult human spinal column consists of more than twenty discrete bones coupled sequentially to one another by a tri-joint complex that consists of an anterior disc and the two posterior facet joints, the anterior discs of adjacent bones being cushioned by cartilage spacers referred to as intervertebral discs. These more than twenty bones are anatomically categorized as being members of one of four classifications: cervical, thoracic, lumbar, or sacral. The cervical portion of the spine, which comprises the top of the spine, up to the base of the skull, includes the first seven vertebrae. The intermediate twelve bones are the thoracic vertebrae, and connect to the lower spine comprising the five lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column is highly complex in that it includes these more than twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes that can result in spinal pathologies for which surgical intervention may be necessary. A variety of systems have been disclosed in the art that achieve immobilization and/or fusion of adjacent bones by implanting artificial assemblies in or on the spinal column. The region of the back that needs to be immobilized, as well as the individual variations in anatomy, determine the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

Referring now to FIGS. 1-2, in which a side perspective view of an intervertebral body cage and an anterior perspective view of a post implantation spinal column are shown, respectively, a more complete description of these devices of the prior art is herein provided. These cages 1 generally comprise tubular metal body 2 having an external surface threading 3. They are inserted transverse to the axis of the spine 4, into preformed cylindrical holes at the junction of adjacent vertebral bodies (in FIG. 14 the pair of cages 1 are inserted between the fifth lumbar vertebra (L5) and the top of the sacrum (S1)). Two cages 1 are generally inserted side by side with the external threading 4 tapping into the lower surface of the vertebral bone above (L5), and the first surface of the vertebral bone (S1) below. The cages 1 include holes 5 through which the adjacent bones are to grow. Additional materials, for example autogenous bone graft materials, may be inserted into the hollow interior 6 of the cage 1 to incite or accelerate the growth of the bone into the cage. End caps (not shown) are often utilized to hold the bone graft material within the cage 1.

These cages of the prior art have enjoyed medical success in promoting fusion and grossly approximating proper disc height. It is, however, important to note that the fusion of the adjacent bones is an incomplete solution to the underlying pathology as it does not cure the ailment, but rather simply masks the pathology under a stabilizing bridge of bone. This bone fusion limits the overall flexibility of the spinal column and artificially constrains the normal motion of the patient. This constraint can cause collateral injury to the patient's spine as additional stresses of motion, normally borne by the now-fused joint, are transferred onto the nearby facet joints and intervertebral discs. It would therefore, be a considerable advance in the art to provide an implant assembly which does not promote fusion, but, rather, which mimics the biomechanical action of the natural disc cartilage, thereby permitting continued normal motion and stress distribution.

It is, therefore, an object of the invention to provide an intervertebral spacer that stabilizes the spine without promoting a bone fusion across the intervertebral space.

It is further an object of the invention to provide an implant device that stabilizes the spine while still permitting normal motion.

It is further an object of the invention to provide a device for implantation into the intervertebral space that does not promote the abnormal distribution of biomechanical stresses on the patient's spine.

It is further an object of the invention to provide an artificial disc that provides free rotation of the baseplates relative to one another.

It is further an object of the invention to provide an artificial disc that supports compression loads.

It is further an object of the invention to provide an artificial disc that permits the baseplates to axially compress toward one another under a compressive load.

It is further an object of the invention to provide an artificial disc that permits the baseplates to axially compress toward one another under a compressive load and restore to their original uncompressed relative positions when the compressive load is relieved.

It is further an object of the invention to provide an artificial disc that prevents lateral translation of the baseplates relative to one another.

It is further an object of the invention to provide an artificial disc that provides a centroid of motion centrally located within the intervertebral space.

It is further an object of the invention to provide artificial intervertebral disc baseplates having outwardly facing surfaces that conform to the concave surface of adjacent vertebral bodies.

It is a further object of the present invention to provide a disc replacement device having a first element for seating against a lower endplate surface of a superior vertebral body and a second element for seating against an first end plate surface of an inferior vertebral body, said baseplates having disposed therebetween a partial spherical member having a large radius disposed in a complementary concavity such that said baseplates are articulatable against one another.

It is yet a further object of the present invention to provide a disc replacement device that is resistant to point loading and fatigue failure.

It is still a further object of the present invention to provide a disc replacement device employing ball and socket type articulation using a partial spherical member wherein said partial spherical member is not captured.

Other objects of the invention not explicitly stated will be set forth and will be more clearly understood in conjunction with the descriptions of the preferred embodiments disclosed hereafter.

SUMMARY OF THE INVENTION

The preceding objects are achieved by the invention, which is an artificial intervertebral disc or intervertebral spacer device comprising a pair of support members (e.g., spaced apart baseplates), each with an outwardly facing surface. Because the artificial disc is to be positioned between the facing endplates of adjacent vertebral bodies, the baseplates are arranged in a substantially parallel planar alignment (or slightly offset relative to one another in accordance with proper lordotic angulation) with the outwardly facing surfaces facing away from one another. The baseplates are to mate with the vertebral bodies so as to not rotate relative thereto, but rather to permit the spinal segments to bend (and in some embodiments, axially compress) relative to one another in manners that mimic the natural motion of the spinal segment. This natural motion is permitted by the performance of a ball and socket type joint using a partial spherical member disposed between the secured baseplates, and the securing of the baseplates to the vertebral bone is achieved through the use of a vertebral body contact element attached to the outwardly facing surface of each baseplate.

Preferable vertebral body contact elements include, but are not limited to, one or more of the following: a convex mesh, a convex solid dome, and one or more spikes. The convex mesh is preferably secured at its perimeter to the outwardly facing surface of the respective baseplate. This can be accomplished in any effective manner, however, laser welding and plasma coating burying are two preferred methods when the mesh is comprised of metal. While domed in its initial undeflected conformation, the mesh deflects as necessary during insertion of the artificial disc between vertebral bodies, and, once the artificial disc is seated between the vertebral bodies, the mesh deforms as necessary under anatomical loads to reshape itself to the concave surface of the vertebral endplate. Thus, the mesh is deformably reshapeable under anatomical loads such that it conformably deflects against the concave surface to securably engage the vertebral body endplate. Stated alternatively, because the mesh is convexly shaped and is secured at its perimeter to the baseplate, the mesh is biased away from the baseplate but moveable toward the plate (under a load overcoming the bias; such a load is present, for example, as an anatomical load in the intervertebral space) so that it will securably engage the vertebral body endplate when disposed in the intervertebral space. This affords the baseplate having the mesh substantially superior gripping and holding strength upon initial implantation, as compared with other artificial disc products. The convex mesh further provides an osteoconductive surface through which the bone may ultimately grow. The mesh preferably is comprised of titanium, but can also be formed from other metals and/or non-metals. Inasmuch as the mesh is domed, it does not restrict the angle at which the artificial disc can be implanted. It should be understood that while the flexible dome is described herein preferably as a wire mesh, other meshed or solid flexible elements can also be used, including flexible elements comprised of non-metals and/or other metals. Further, the flexibility, deflectability and/or deformability need not be provided by a flexible material, but can additionally or alternatively be provided mechanically or by other means.

It should be understood that the convex mesh attachment devices and methods described herein can be used not only with the artificial discs and artificial disc baseplates described or referred to herein, but also with other artificial discs and artificial disc baseplates, including, but not limited to, those currently known in the art. Therefore, the description of the mesh attachment devices and methods being used with the artificial discs and artificial disc baseplates described or referred to herein should not be construed as limiting the application and/or usefulness of the mesh attachment device.

To enhance the securing of the baseplates to the vertebral bones, each baseplate further comprises a porous area, which at least extends in a ring around the lateral rim of each outwardly facing surface. The porous area may be, for example, a sprayed deposition layer, or an adhesive applied beaded metal layer, or another suitable porous coating known in the art. The porous ring permits the long-term ingrowth of vertebral bone into the baseplate, thus permanently securing the prosthesis within the intervertebral space. The porous layer may extend beneath the domed mesh as well, but is more importantly applied to the lateral rim of the outwardly facing surface of the baseplate that seats directly against the vertebral body.

Some of the embodiments described herein use two baseplates each having the above described convex mesh on its outwardly facing surface, while other embodiments use two baseplates each having a convex solid dome in combination with a plurality of spikes on the lateral rim of the outwardly facing surface of the baseplates. It should be understood, however, that the various attachments devices or methods described herein (as well as any other attachment devices or methods, such as, for example, keels) can be used individually or in combination in any permutation, without departing from the scope of the present invention.

The ball and socket joint, employing a partial spherical member that is not captured, disposed between the baseplates permits rotation and angulation of the two baseplates relative to one another about a centroid of motion centrally located between the baseplates. A variety of embodiments are contemplated. In some embodiments, the joint is used in conjunction with a resilient member to additionally permit the two baseplates to axially compress relative to one another. Further in each of the embodiments, the assembly prevents lateral translation of the baseplates during rotation and angulation.

It should be understood that the described embodiments and embodiment families are merely examples that illustrate aspects and features of the present invention, and that other embodiments and embodiment families are possible without departing from the scope of the invention.

Each of the embodiments discussed herein share the same basic elements, some of which retain identical functionality and configuration across the embodiments, and some of which gain or lose functionality and/or configuration across the embodiments to accommodate mechanical and/or manufacturing necessities. More specifically, each of the embodiments includes two baseplates, each having an inwardly directed articulation surface, having a ball and socket joint disposed therebetween employing an uncaptured partial spherical member that is established centrally between the baseplates. The partial spherical member has a large radius and substantially continuous arc of curvature to minimize point loading and reduce the risk and incidence of fatigue failure. Each of the embodiments will be understood further in light of the additional descriptions of the embodiments herein.

The inwardly directed articulation surface of the first baseplate is adapted such that extending thereform is a member having at its distal end a partial spherical member. The partial spherical member is defined by a convex arc that forms the articulation surface that is complementary to a concave articulation surface of the second baseplate.

In a preferred embodiment the longitudinally inwardly directed articulation surface of the first baseplate comprises essentially a centrally disposed projection having a central bore for receiving and/or retaining an elongated member. The projection is sized to have a diameter less than the diameter of the inwardly directed concave articulating surface of the second baseplate. The projection preferably has a cross section that is cylindrical or frustoconical.

In a preferred embodiment, the elongated member comprises essentially a mushroom-shaped pin having an elongated portion and a head portion, the elongated portion thereof seated in a central bore of the first baseplate and the head portion, located distally, having a convex arc having a substantially constant radius of curvature A. The pin shaped member may be fixedly engaged in the bore or may be slidably engaged in the bore. In the embodiment in which the pin is slidably engaged in the bore, in a preferred embodiment a resilient annular member such as a resilient washer or the like is optionally deployed over the projection of the first baseplate as a shock absorber, the resilient annular member being positioned with one side facing the surface adjacent the projection of the first member and the opposite side of the annular resilient member facing the interior of the head of the pin-shaped member.

The elongated portion of the pin member preferably comprises a continuous cylindrical cross section; however, the cross section may vary toward the distal end thereof, such as by gradually or abruptly thickening near the juncture of the elongated member and the head portion, to provide structural strength.

The longitudinally inwardly directed articulation surface of the second baseplate is a substantially constant radii concave articulation surface forming a curvate socket.

The constant radii articulation surfaces are configured and sized to be nestable against one another and articulatable against one another, to enable adjacent vertebral bones (against which the first and second baseplates are respectively disposed in the intervertebral space) to articulate in flexion, extension, and lateral bending. More particularly, the artificial disc implant of the present invention is assembled by disposing the first and second baseplates such that the vertebral body contact surfaces are directed away from one another, and the articulation surfaces are nested against one another such that the concave arc accommodates the convex arc.

The curvate socket defines a spherical contour that closely accommodates the partial spherical member for free rotation and angulation. Therefore, when seated in the curvate socket, the partial spherical member can rotate and angulate freely relative to the curvate socket through a range of angles, thus permitting the opposing baseplates to rotate and angulate freely relative to one another through a corresponding range of angles equivalent to the fraction of normal human spine rotation and angulation (to mimic normal disc rotation and angulation). Because the baseplates are made angulatable relative to one another by the partial spherical member being rotatably and angulatably coupled in the curvate socket, the disc assembly provides a centroid of motion within the sphere defined by the partial spherical member. Accordingly, the centroid of motion of the disc assembly remains centrally located between the vertebral bodies, similar to the centroid of motion in a healthy natural intervertebral disc.

Optionally, the end of the mushroom-shaped pin element proximal to the baseplate, and the bore in which it is located, may be covered by a vertebral body contact element disposed on or as the outside surface of the baseplate. In such an embodiment it is preferable to include such a vertebral body contact element disposed on or as the opposing baseplate for purposes of symmetry. Such contact elements are preferably contoured to match the contour of the surface it contacts in the intervertebral space.

In other preferred embodiments of the present invention, an intervertebral device includes a first plate having an outer face and an inner face, and a second plate juxtaposed with the first plate, the second plate having an outer face, an inner face that opposes the first plate and a concavity that opposes the first plate. The device preferably includes an elongated member extending from the first plate toward the second plate, the elongated member having a distal end with a spherical surface that is engageable with the concavity of the second plate for providing an articulating joint between the first and second plates. The device also desirably includes a resilient member in contact with the elongated member for counteracting compressive loads on the plates, whereby the resilient member is surrounded by the concavity of the second plate.

In other preferred embodiments of the present invention, an intervertebral device includes a first plate having an outer face and an inner face, a second plate juxtaposed with the first plate, the second plate having an outer face and an inner face that opposes the first plate, and a ball and socket articulating joint provided between the first and second plates. The device also preferably includes a resilient member in contact with the ball portion of the ball and socket articulating joint for counteracting compressive loads on the plates, whereby the resilient member extends between the first and second plates and is surrounded by the socket portion of the articulating joint.

In still other preferred embodiments of the present invention, an intervertebral device includes a first plate having an outer face and an inner face, a second plate juxtaposed with the first plate, the second plate having an outer face and an inner face that opposes the first plate, the inner face of the second plate having a concavity, and an elongated member extending from the inner face of the first plate toward the second plate, the elongated member being slideably attached to the first plate and having a distal end with a spherical surface that forms a ball and socket-like articulating joint between the first and second plates. The device may also include a resilient member in contact with the distal end of the elongated member for counteracting compressive loads on the plates. The concavity of the second plate desirably surrounds the resilient member. The elongated member may have a mushroom-shaped head at the distal end thereof.

These and other preferred embodiments of the present invention will be described in more detail below.

DETAILED DESCRIPTION

While the invention will be described more fully hereinafter with reference to the accompanying drawings, in which particular embodiments and methods of implantation are shown, it is to be understood at the outset that persons skilled in the art may modify the invention herein described while achieving the functions and results of the invention. Accordingly, the descriptions that follow are to be understood as illustrative and exemplary of specific structures, aspects and features within the broad scope of the invention and not as limiting of such broad scope. Like numbers refer to similar features of like elements throughout.

A preferred embodiment of the present invention will now be described.

Figure 1:
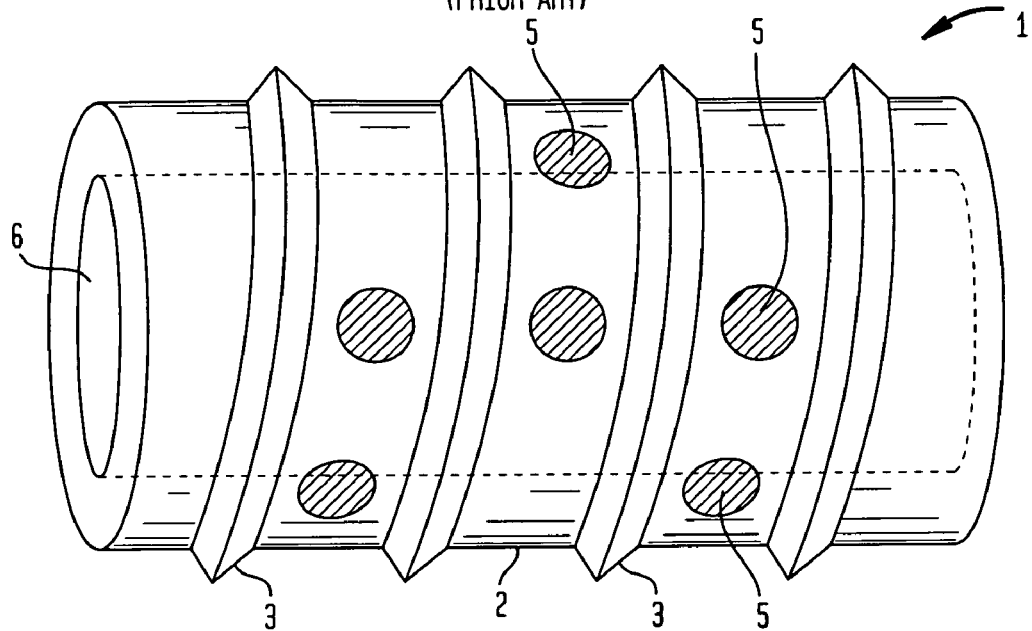
FIG. 1 shows a side perspective view of a prior art interbody fusion device.
Figure 2:
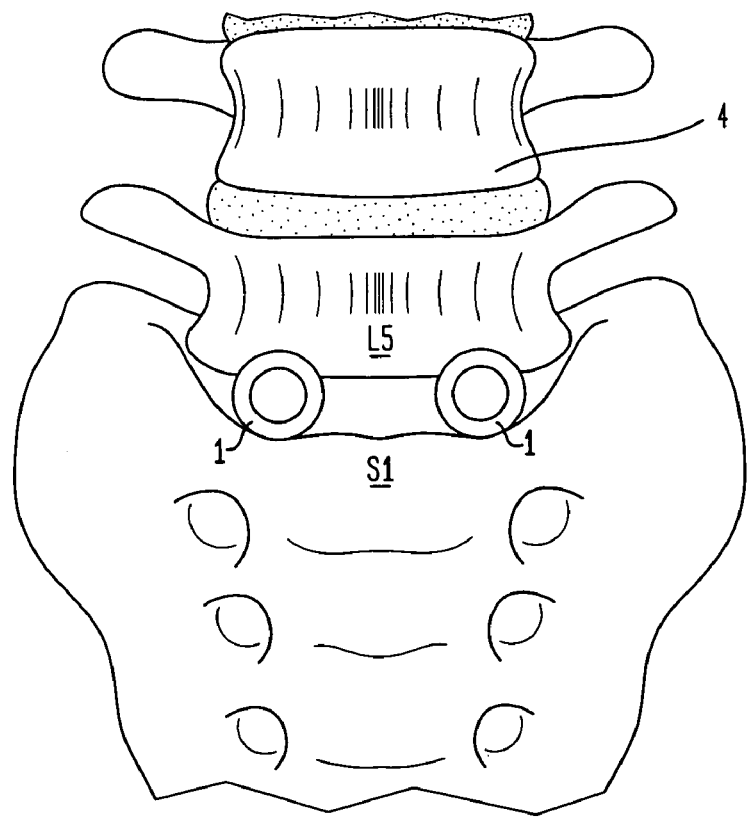
FIG. 2 shows a front view of the anterior portion of the lumbo-sacral region of a human spine, into which a pair of interbody fusion devices of FIG. 1 have been implanted.
Figure 3:
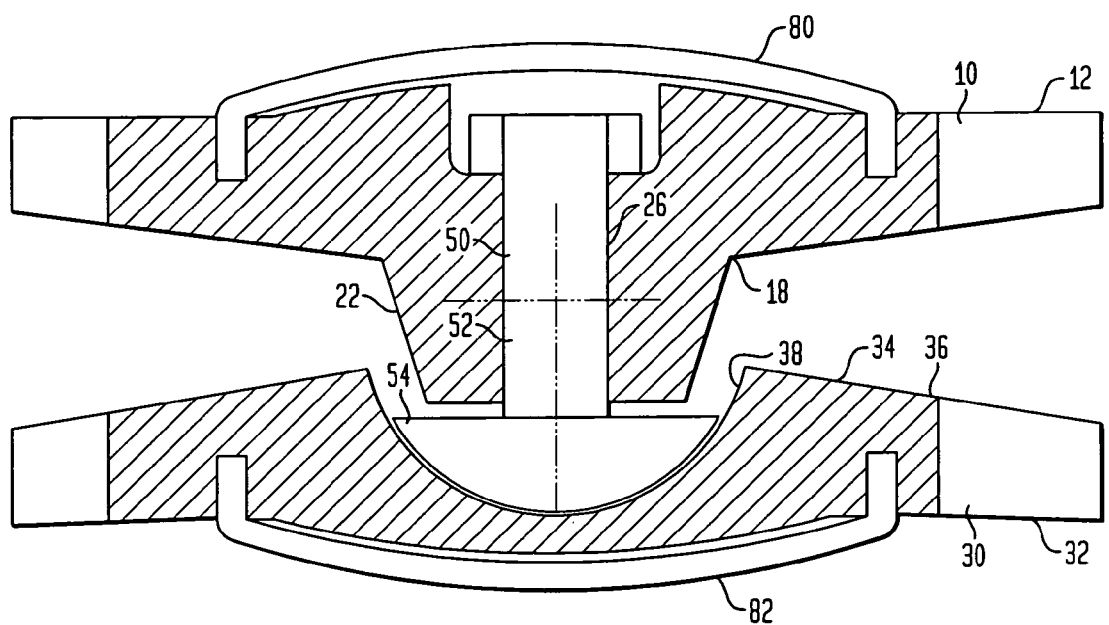
FIG. 3 is a cross sectional view of a first embodiment of the present invention, the first baseplate having an inwardly directed articulating surface having extending therefrom a mushroom-shaped pin element having a partial spherical element at the distal end thereof and a second baseplate having a circular recess within which seats the convex structure of the partial spherical element of the first baseplate.

Referring to FIG. 3, the invention is shown having a first baseplate 10 and a second baseplate 30 and a pin 50. Each baseplate 10,30 has an outwardly facing surface 12,32. Because the artificial disc of the invention is to be positioned between the facing surfaces of adjacent vertebral bodies, the two baseplates 10,30 used in the artificial disc are disposed such that the outwardly facing surfaces 12,32 face away from one another. The two baseplates 10,30 are to mate with the vertebral bodies so as to not rotate relative thereto, but rather to permit the spinal segments to bend relative to one another in manners that mimic the natural motion of the spinal segment. This motion is permitted by the performance of a ball and socket joint disposed between the secured baseplates 10,30. The mating of the baseplates 10,30 to the vertebral bodies and the construction of the ball and socket joint are described below.

More particularly, each baseplate 10,30 is a plate (preferably made of a metal or metal alloy, such as, for example, cobalt-chromium or titanium) having an overall shape that conforms to the overall shape of the respective endplate of the vertebral body with which it is to mate. Further, each baseplate 10,30 comprises a vertebral body contact element 80,82 (e.g., a convex mesh, preferably oval in shape) that is attached to the outwardly facing surface 12,32 of the baseplate 10,30 to provide a vertebral body contact surface. The mesh 80,82 is secured at its perimeter to the outwardly facing surface 12,32 of the baseplate 10,30. The mesh 80,82 is domed in its initial undeflected conformation, but deflects as necessary during insertion of the artificial disc between vertebral bodies, and, once the artificial disc is seated between the vertebral bodies, deforms as necessary under anatomical loads to reshape itself to the concave surface of the vertebral endplate. This affords the baseplate 10,30 having the mesh 80,82 substantially superior gripping and holding strength upon initial implantation as compared with other artificial disc products. The mesh 80,82 further provides an osteoconductive surface through which the bone may ultimately grow. The mesh 80,82 is preferably comprised of titanium, but can also be formed from other metals and/or non-metals without departing from the scope of the invention.

Each baseplate 10,30 may further comprises at least a lateral ring (not shown) that is osteoconductive, which may be, for example, a sprayed deposition layer, or an adhesive applied beaded metal layer, or another suitable porous coating. This porous ring permits the long-term ingrowth of vertebral bone into the baseplate 10,30, thus permanently securing the prosthesis within the intervertebral space. It shall be understood that this porous layer may extend beneath the domed mesh 80,82 as well, but is more importantly applied to the lateral rim of the outwardly facing surface 12,32 of the baseplate 10,30 that seats directly against the vertebral body.

Each of the baseplates 10,30 comprises features that, in conjunction with other components described below, form the ball and socket joint. The first baseplate 10 includes an inwardly facing articulating surface 18 that includes a perimeter region 20 and a projection 22 protruding from the inwardly facing surface 18. The projection 22 preferably has a cylindrical or frustoconical cross section. The projection 22 further includes an axial bore 26 that accepts a mushroom-shaped pin 50 (or rivet, plug, dowel, or screw).

The second baseplate 30 comprises an inwardly facing articulation surface 34 having a peripheral surface 36 and a curvate socket 38, the socket 38 having a substantially constant radii concave articulation surface.

Pin 50 further comprises an elongated portion 52 and a head 54, the head 54 having a convex arc having a substantially constant radius of curvature. The arc of head 54 is such that the sphere it defines has a large radius, thereby minimizing point loading and the risk of fatigue failure.

The projection 22 of baseplate 10 is sized to have a diameter at least a portion of which is less than the diameter of the socket 38. The projection 22 preferably has a cross section that is cylindrical or frustoconical.

In a first embodiment, the elongated portion 52 of mushroom-shaped pin 50 is disposed in bore 26 of the baseplate 10 and the head 54 is nested in socket 38. Pin 50 is fixedly engaged by force fitting, welding or the like in bore 26. Head 54 is not captured in socket 38. Baseplates 10 and 30 are at no time connected to each other in the ball and socket joint of the present invention.

Optionally, the end of pin 50 proximal to the baseplate 10, and the bore 26, are covered by a vertebral body contact element 80 disposed over the outside surface 12 of the baseplate 10. In such an embodiment it is preferable to include a vertebral body contact element 82 on the baseplate 30 for purposes of symmetry. Such contact elements 80 and 82 are preferably contoured to match the contour of the surface it contacts in the intervertebral space.

Figure 4:
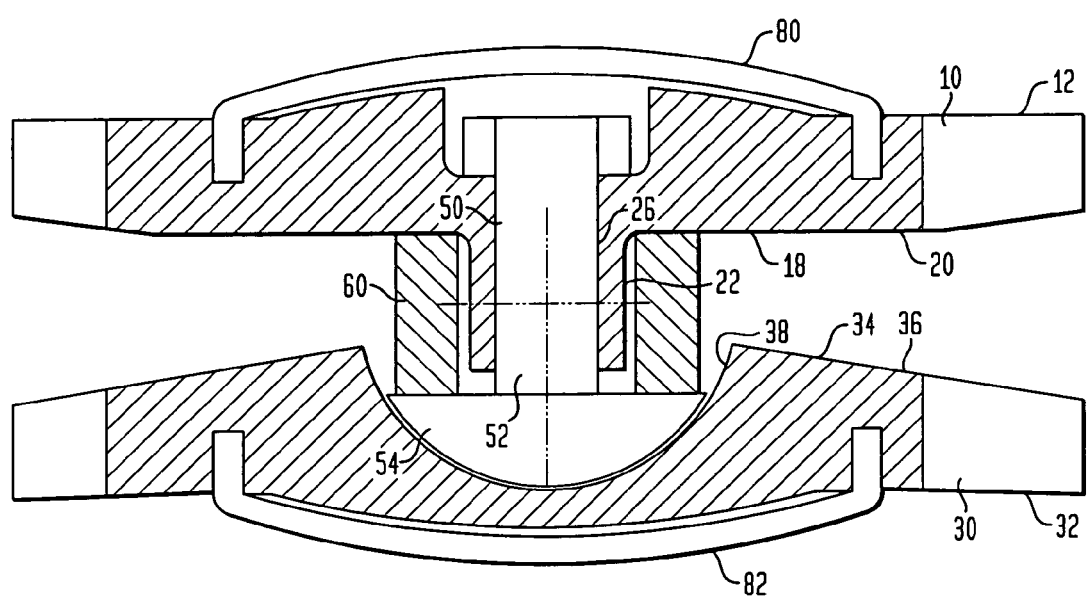
FIG. 4 is a cross-sectional view of a second embodiment of the present invention in which the pin element is slidably engaged in a central bore of the first baseplate and further includes a resilient member disposed between the first and second baseplates.

Now referring to FIG. 4, in a preferred embodiment, pin 50 is slidably engaged in bore 26. In this embodiment, in a preferred embodiment a resilient annular member 60 such as a resilient washer or the like is deployed over the projection 22 (which in this embodiment is preferably cylindrical) of the first baseplate 10 as a shock absorber, the resilient annular member 60 being sized and positioned such that it functions as a force restoring element (e.g., a spring) that provides axial cushioning to the device, by deflecting under a compressive load and restoring when the load is relieved.

Figure 5:
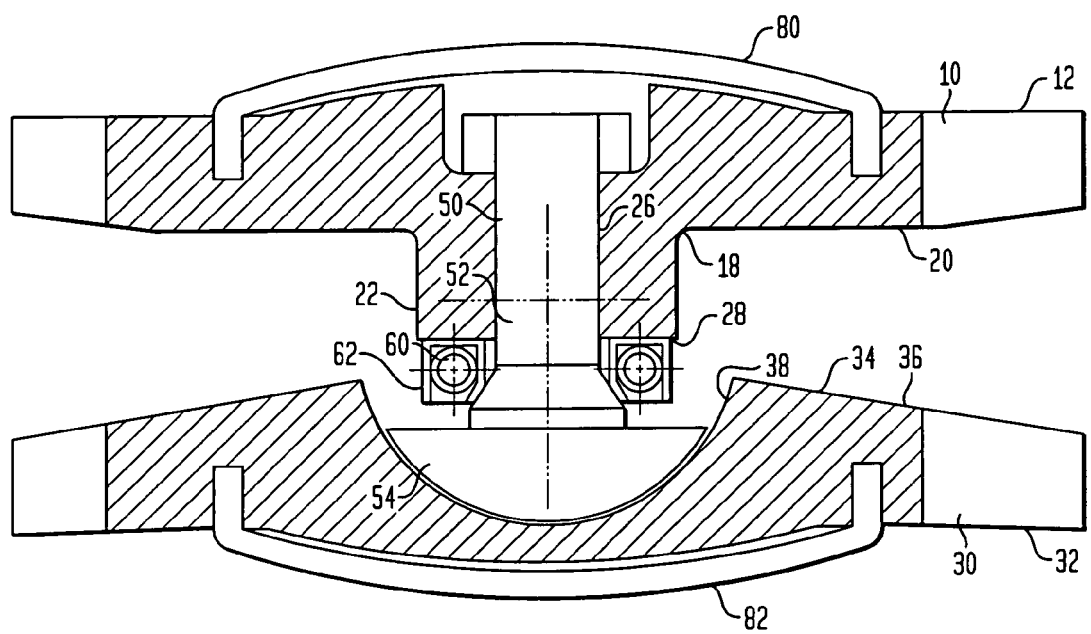
FIG. 5 is a cross-sectional view of a preferred embodiment of the present invention.
Figure 6:
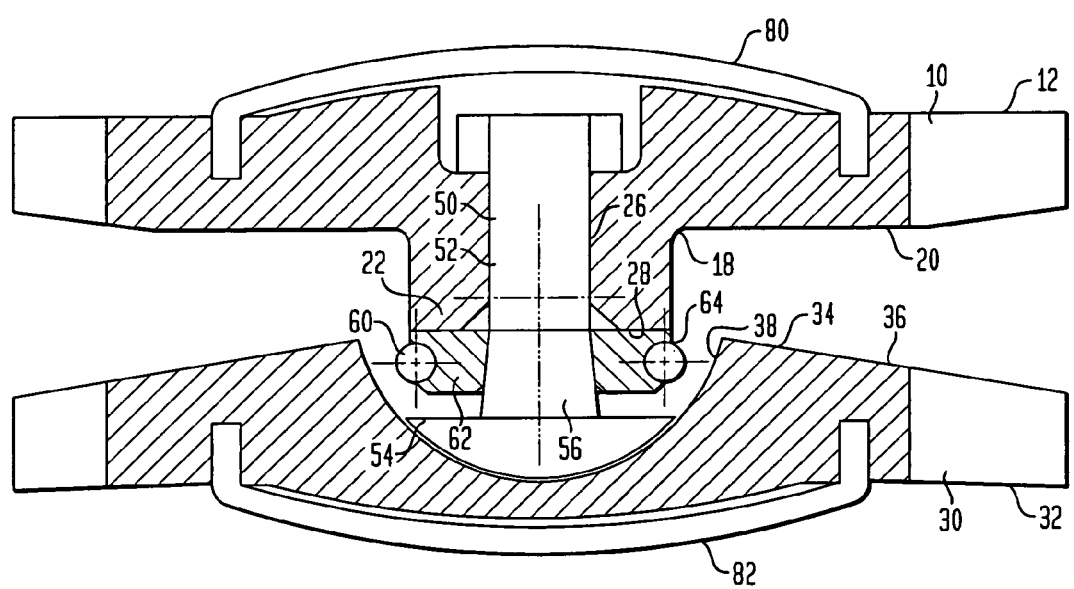
FIG. 6 is a cross-sectional view of a preferred embodiment of the present invention.

Now referring to FIGS. 5 and 6, in other embodiments the elongated portion 52 of pin 50 preferably has a continuous cylindrical cross section; however, the cross section may vary toward the distal end thereof, such as by gradually or abruptly thickening near the juncture of the elongated member 52 and the head 54, to provide structural strength and/or to provide a different location for resilient member 60. Now referring to FIG. 5, in a preferred embodiment resilient member 60 is a continuous collar comprising a spring having a cylindrical cross section. It is desirable, but not essential, to use a spring as the resilient member 60 because of the ability of a spring to hold its diameter when subjected to compressive force. In a most preferred embodiment resilient member 60 is retained in a retainer 62. Retainer 62 is formed of a resilient material such as but not limited to an elastomeric material. In this embodiment elongated member 52 has a frustoconical section 56 adjacent proximal head 54 such that resilient member 60 and retainer 62 are firmly engageable in a seat formed between the frustoconical section 56 of elongated portion 52 and the end 28 of projection 22. As forces are applied to retainer 62, the spring comprising resilient member 60 deforms outwardly such that its diameter increases.

In another embodiment, now referring to FIG. 6, resilient member 60 is an O-ring preferably formed of an elastomeric material. Retainer 62 is a collar such as a split collar having formed thereon an exterior groove 64 to accommodate secure mounting of a resilient member 60. In this embodiment elongated member 52 has a frustoconical section 56 adjacent proximal head 54 such that resilient member 60 and retainer 62 are firmly engageable between the frustoconical section 56 of elongated portion 52 and the end 28 of projection 22. As forces are applied to retainer 62, the O-ring comprising resilient member 60 deforms outwardly such that its diameter increases.

The substantially constant radii articulation surfaces of the head 54 and socket 38 are configured and sized to be nestable against one another and articulatable against one another, to enable adjacent vertebral bones (against which the baseplates 10 and 30 are respectively disposed in the intervertebral space) to articulate in flexion, extension, and lateral bending. More particularly, the artificial disc implant of the present invention is assembled by disposing the baseplates 10 and 30 such that the vertebral body contact surfaces 80,82 are directed away from one another, and the articulation surfaces (head 54 and socket 38) are nested against one another such that the concave arc of socket 38 accommodates the convex arc of head 54.

While there has been described and illustrated specific embodiments of an artificial disc, it will be apparent to those skilled in the art that variations and modifications are possible without deviating from the broad spirit and principle of the invention. The invention, therefore, shall not be limited to the specific embodiments discussed herein.

The invention claimed is:

1. An intervertebral device comprising:
a first baseplate having a bore;
a second baseplate juxtaposed with the first baseplate, the second baseplate having an articulation surface;
a pin having an elongated portion slidable within the bore and a head nested with the articulation surface; and
a resilient member engaged with the first baseplate and the pin for counteracting movement of the elongated portion within the bore.

2. The intervertebral device of claim 1, wherein the articulation surface is a concave surface and the head includes a convex surface.

3. The intervertebral device of claim 1, wherein the first baseplate includes a projection that extends toward the second baseplate, the projection including at least a portion of the bore.

4. The intervertebral device of claim 3, wherein the resilient member extends at least partially around the projection.

5. The intervertebral device of claim 3, wherein the resilient member is in contact with the projection.

6. The intervertebral device of claim 3, wherein the resilient member extends between the projection and a portion of the pin.

7. The intervertebral device of claim 6, wherein the resilient member extends between the projection and an enlarged portion of the elongated portion.

8. The intervertebral device of claim 1, wherein the resilient member is ring-shaped.

9. The intervertebral device of claim 1, wherein the resilient member is a spring.

10. The intervertebral device of claim 1, wherein the resilient member is an o-ring.

11. The intervertebral device of claim 1, wherein the resilient member extends between the first baseplate and the head.

12. The intervertebral device of claim 1, wherein the resilient member is retained in a retainer.

13. The intervertebral device of claim 12, wherein the retainer is formed of a resilient material.

14. The intervertebral device of claim 1, wherein the first baseplate includes a first vertebral body contact element and the second baseplate includes a second vertebral body contact element.

15. The intervertebral device of claim 14, wherein the first vertebral body contact element covers the bore.

16. An intervertebral device comprising:
a first baseplate having a projection, a bore, and a first vertebral contact element covering the bore;
a second baseplate juxtaposed with the first baseplate, the second baseplate having an articulation surface and a second vertebral contact element;
a pin having an elongated portion slidable within the bore and a head nested with the articulation surface, the elongated portion including an enlarged portion; and
a resilient member extending between the projection and the enlarged portion of the elongated portion for counteracting movement of the elongated portion within the bore.

17. The intervertebral device of claim 16, wherein the articulation surface is a concave surface and the head includes a convex surface.

18. The intervertebral device of claim 16, wherein the resilient member is a spring.

19. The intervertebral device of claim 16, wherein the resilient member is an o-ring.

20. An intervertebral device comprising:
a first baseplate having a projection, a bore, and a first vertebral contact element covering the bore;
a second baseplate juxtaposed with the first baseplate, the second baseplate having an articulation surface and a second vertebral contact element;
a pin having an elongated portion slidable within the bore and a head nested with the articulation surface; and
a resilient member disposed at least partially around the projection and extending between the first baseplate and the head for counteracting movement of the elongated portion within the bore.

21. The intervertebral device of claim 20, wherein the articulation surface is a concave surface and the head includes a convex surface.

22. The intervertebral device of claim 16, wherein the resilient member is a resilient washer.

* * * * *